(12) United States Patent
Ding et al.

(10) Patent No.: US 11,851,692 B2
(45) Date of Patent: Dec. 26, 2023

(54) METHOD FOR PREPARING AN ANTIMYCIN COMPOUND PRODUCED BY *STREPTOMYCES* SP.4-7

(71) Applicant: Ningbo University, Ningbo (CN)

(72) Inventors: Lijian Ding, Ningbo (CN); Shan He, Ningbo (CN); Wenhao Li, Ningbo (CN); Weiyan Zhang, Ningbo (CN); Yingying Wei, Ningbo (CN)

(73) Assignee: NINGBO UNIVERSITY, Ningbo (CN)

( * ) Notice: Subject to any disclaimer, the term of this patent is extended or adjusted under 35 U.S.C. 154(b) by 0 days.

(21) Appl. No.: 18/127,674

(22) Filed: Mar. 29, 2023

(65) Prior Publication Data

US 2023/0313247 A1     Oct. 5, 2023

(30) Foreign Application Priority Data

Mar. 29, 2022   (CN) .......................... 202210315388.9

(51) Int. Cl.
   *C12P 17/08*     (2006.01)
   *C07D 321/00*    (2006.01)

(52) U.S. Cl.
   CPC ............ *C12P 17/08* (2013.01); *C07D 321/00* (2013.01)

(58) Field of Classification Search
   None
   See application file for complete search history.

(56) References Cited

FOREIGN PATENT DOCUMENTS

| CN | 101701233 | A | | 5/2010 |
|---|---|---|---|---|
| CN | 104418833 | A | | 3/2015 |
| CN | 111411062 | A | | 7/2020 |
| CN | 114380764 | A | * | 4/2022 |
| CN | 114380814 | A | * | 4/2022 |
| CN | 114957198 | A | * | 8/2022 |

OTHER PUBLICATIONS

Li et al., "Novel Antimycin Analogues with Agricultural Antifungal Activities from the Sponge-Associated Actinomycete *Streptomyces* sp. NBU3104", J. Agric. Food Chem. 70:8309-8316, Jun. 2022 (Year: 2022).*
Translation of CN 114957198 A, obtained from Google Patents on Jul. 20, 2023 (Year: 2023).*
Translation of CN 114380814 A, obtained from Google Patents on Jul. 20, 2023 (Year: 2023).*
Translation of CN 114380764 A, obtained from Google Patents on Jul. 20, 2023 (Year: 2023).*
Jianxin Zhou, et al., Grain and Food Microbiology, 2023, pp. 53,58, Chemical Industry Press.
Nutrition and Food Hygiene, 2000, pp. 123-125.

* cited by examiner

*Primary Examiner* — David Steadman
(74) *Attorney, Agent, or Firm* — Bayramoglu Law Offices LLC (57) ABSTRACT

Disclosed are an antimycin compound and a preparation method and use thereof. The preparation method comprises: fermenting a marine actinomycete (*Streptomyces* sp.4-7) with a preservation number CCTCCNO: M2020953 to obtain a fermented product and soaking and extracting the fermented product with ethyl acetate to obtain a crude extract; and carrying out separation and purification by normal-phase silica gel column chromatography, reversed-phase MPLC, and semi-preparative reversed-phase high-performance liquid chromatography. The invention has the advantages of resistance against *Botrytis cinerea* and *Penicillium citrinum*.

1 Claim, 9 Drawing Sheets

METHOD FOR PREPARING AN ANTIMYCIN COMPOUND PRODUCED BY *STREPTOMYCES* SP.4-7

CROSS REFERENCE TO RELATED APPLICATIONS

This application is based upon and claims priority to Chinese Patent Application No. 202210315388.9, filed on Mar. 29, 2022, the entire contents of which are incorporated herein by reference.

TECHNICAL FIELD

The present invention relates to antimycin compounds, in particular to an antimycin compound and a preparation method and use thereof.

BACKGROUND

Antimycin compounds are a type of natural products, and they have a common structural skeleton, which consists of a macrocycle connected to a 3'-carboxamide salicylic acid unit through an amide bond. These compounds are usually isolated from actinomycetes and have great structural diversity based on the size of the macrocycle (9-, 12-, 15- or 18-membered ring) and substituents on the ring. Since they were first isolated in 1949, antimycin compounds have attracted great attention due to their powerful and diverse biological activities. In particular, antimycin compounds have been proven to have antifungal, insecticidal, nematicidal and piscicidal activities due to their ability to inhibit the mitochondrial electron transport chain. Recently, several types of antimycin-type compounds have also been proven to have good anticancer and anti-inflammatory activities.

In the chemical investigation of the ethyl acetate extract of a marine actinomycete strain-*Streptomyces* sp.4-7 fermented in a YMG medium, a new natural product of antimycin, named Antimycin I, was found, and its secondary metabolites were further isolated, purified and evaluated for activity. There is no report on the chemical structure and activity of this compound at present, so there is no drug related to it in the market.

SUMMARY

The technical problem to be solved by the present invention is to provide an antimycin compound and a preparation method and use thereof. The antimycin compound has inhibitory effect on *Botrytis cinerea* and *Penicillium citrinum*.

To solve above technical problems, the following technical solutions are adopted in the present invention.

1. An antimycin compound of formula (1), isolated from secondary metabolites of a marine actinomycete;

2. A preparation method of an antimycin compound, comprising the following steps:

(1) Fermentation Production streaking a marine actinomycete (*Streptomyces* sp.4-7) with a preservation number CCTCCNO: M2020953 on a plate of GAUZE's solid medium No. 1, incubating and activating-*Streptomyces* sp.4-7 in a 28° C. incubator for 7 days, picking and inoculating single colonies in GAUZE's liquid medium No. 1, placing the GAUZE's liquid medium No. 1 on a shaker for incubation and proliferation at a temperature of 28° C. and a speed of 180 rpm/min; after 3 days of incubation, collecting seed liquid, and then inoculating the seed liquid into a YMG medium at an inoculation dose of 10% by volume and carrying out incubation at 28° C. for 11 days to obtain a fermented product;

(2) Extraction adding ethyl acetate to the fermented product obtained in step (1), wherein the volume of ethyl acetate added is equal to the volume of the fermented product; carrying out extraction for 3 times, combining ethyl acetate phases obtained from the three extractions, concentrating the ethyl acetate extract under reduced pressure and evaporating the concentrated ethyl acetate extract to dryness to obtain a crude extract; and (3) Separation and Preparation of a Compound first dissolving the crude extract obtained in step (2) in a mixed solvent of dichloromethane and methanol with a volume ratio of 1:1, and then mixing the resulting solution with 200-300-mesh silica gel to obtain a sample, carrying out normal-phase medium-pressure liquid chromatography (MPLC) with gradient elution by using an eluent petroleum ether-ethyl acetate solution with volume ratios of (100:1)-(0:1), and collecting and arranging eluted fractions in order according to the polarity of the fractions from low to high and combining the fractions to obtain 6 fractions; carrying out reversed-phase MPLC with gradient elution on the collected second fraction by using an eluent acetonitrile-water solution with volume ratios of 30-100%, collecting and arranging eluted fractions in order according to the polarity of the fractions from high to low and combining the fractions to obtain 21 fractions; and separating and purifying the collected 9th fraction by semi-preparative reversed-phase high-performance liquid chromatography using a mixed solution of acetonitrile and water with a volume ratio of 24:76 as a mobile phase, thus obtaining a compound of formula (I), The YMG medium described in step (1) is prepared by dissolving 20 g of starch, 10 g of glucose, 5 g of yeast extract, 5 g of malt extract, 0.5 g of calcium carbonate and 30 g of sea salt in 1000 mL of seawater.

In the reversed-phase MPLC with gradient elution described in step (3), The volume percentage of acetonitrile is within a range of 30% to 100%, and the elution time is 150 min.

The flow rate in the separation and preparation of the compound by semi-preparative reversed-phase high performance liquid chromatography in step (3) is 2.0 mL/min.

3. Use of the antimycin compound in preparation of an inhibitor of *Botrytis cinerea* and/or *Penicillium citrinum*.

Compared with the prior art, the present invention has the following advantages: according to an antimycin compound of the present invention and a preparation method and use thereof, an antimycin compound is isolated from a secondary metabolite of a marine actinomycete (*Streptomyces* sp.4-7). microbial fermentation culture is carried out to obtain the fermented product of the antimycin compound and then the fermented product is soaked and extracted with ethyl acetate to obtain a crude extract. The crude extract is separated and purified by normal-phase medium-pressure silica gel column chromatography, reversed-phase MPLC, and semi-preparative reversed-phase high-performance liquid chromatography. Through antifungal activity screening, it is found that the compound has significant resistance activity against *Botrytis cinerea* and *Penicillium citrinum*, and can be used in the development of lead drugs for inhibiting related plant diseases caused by *Botrytis cinerea* and *Penicillium citrinum*.

The marine actinomycete (*Streptomyces* sp.4-7) with a preservation number CCTCCNO: M2020953 was preserved in the China Center for Type Culture Collection on Dec. 21, 2020 at College of Life Sciences Wuhan University, Wuhan city 430072 China.

DETAILED DESCRIPTION OF THE INVENTION

With reference to the embodiments, the present invention will be further described in detail below in connection with the drawing.

Example 1

Provided was an antimycin compound of formula (I) obtained by fermenting a marine actinomycete (*Streptomyces* sp.4-7):

Example 2

Provided was a preparation method of the antimycin compound of formula (I), specifically comprising the following steps.

1. Fermentation Production

A marine actinomycete (*Streptomyces* sp.4-7) with a preservation number CCTCCNO: M2020953 was streaked on a plate of GAUZE's solid medium No. 1, incubated and activated in a 28° C. incubator for 7 days. Single colonies were picked and inoculated in GAUZE's liquid medium No. 1, then placed on a shaker for incubation and proliferation at a temperature of 28° C. and a speed of 180 rpm/min. After 3 days of incubation, seed liquid was collected and then inoculated into a YMG medium at an inoculation dose of 10% by volume and incubated at 28° C. for 11 days to obtain a fermented product. The GAUZE's solid medium No. 1 was prepared by dissolving 20 g of soluble starch, 1 g of $KNO_3$, 0.5 g of $K_2HPO_4$, 0.5 g of $MgSO_4 \cdot 7H_2O$, 5 g of NaCl, 0.01 g of $FeSO_4 \cdot 7H_2O$ and 20 g of agar in 1000 mL of distilled water and adjusting the pH value to a range of 7.4 to 7.6. The GAUZE's liquid medium No. 1 was prepared by dissolving 20 g of soluble starch, 1 g of $KNO_3$, 0.5 g of $K_2HPO_4$, 0.5 g of $MgSO_4 \cdot 7H_2O$, 0.5 g of NaCl, and 0.01 g of $FeSO_4 \cdot 7H_2O$ in 1000 mL of distilled water and adjusting the pH value to a range of 7.4 to 7.6. The YMG medium was prepared by dissolving 20 g of starch, 10 g of glucose, 5 g of yeast extract, 5 g of malt extract, 0.5 g of calcium carbonate and 30 g of sea salt in seawater.

(2) Extraction

Ethyl acetate was added to the fermented product obtained in step (1), wherein the volume of ethyl acetate added was equal to the volume of the fermented product. Extraction was carried out repeatedly for 3 times. Ethyl acetate phases obtained from the three extractions were combined, and the ethyl acetate extract was concentrated under reduced pressure and evaporated to dryness to obtain a crude extract.

(3) Separation and Preparation of the Compound

The crude extract obtained in step (2) was first dissolved in a mixed solvent of dichloromethane and methanol with a volume ratio of 1:1, and then the resulting solution was mixed with 200-300-mesh silica gel to obtain a sample. Normal-phase medium-pressure column chromatography with gradient elution by using an eluent petroleum ether-ethyl acetate solution with volume ratios of 100:1, 10:2, 10:3, 10:4, 10:5 and 0:1 was carried out. Eluted fractions were then collected and arranged in order according to the polarity of the fractions from low to high and combined to obtain 6 fractions. Reversed-phase MPLC with gradient elution was carried out on the collected second fraction (in the case of the eluent petroleum ether-ethyl acetate solution with a volume ratio of 10:2), linear elution by using an eluent acetonitrile-water solution with a volume ratio of 30-100% was carried out for 150 min, and eluted fractions were collected and arranged in order according to the polarity of the fractions from high to low and combined to obtain 21 fractions. The collected 9th fraction was separated and purified by semi-preparative reversed-phase high-performance liquid chromatography using a mixed solution of acetonitrile and water with a volume ratio of 24:76 as a mobile phase at a flow rate of 2.0 mL/min, thus obtaining the compound of formula (I), (I)

Figure 1:
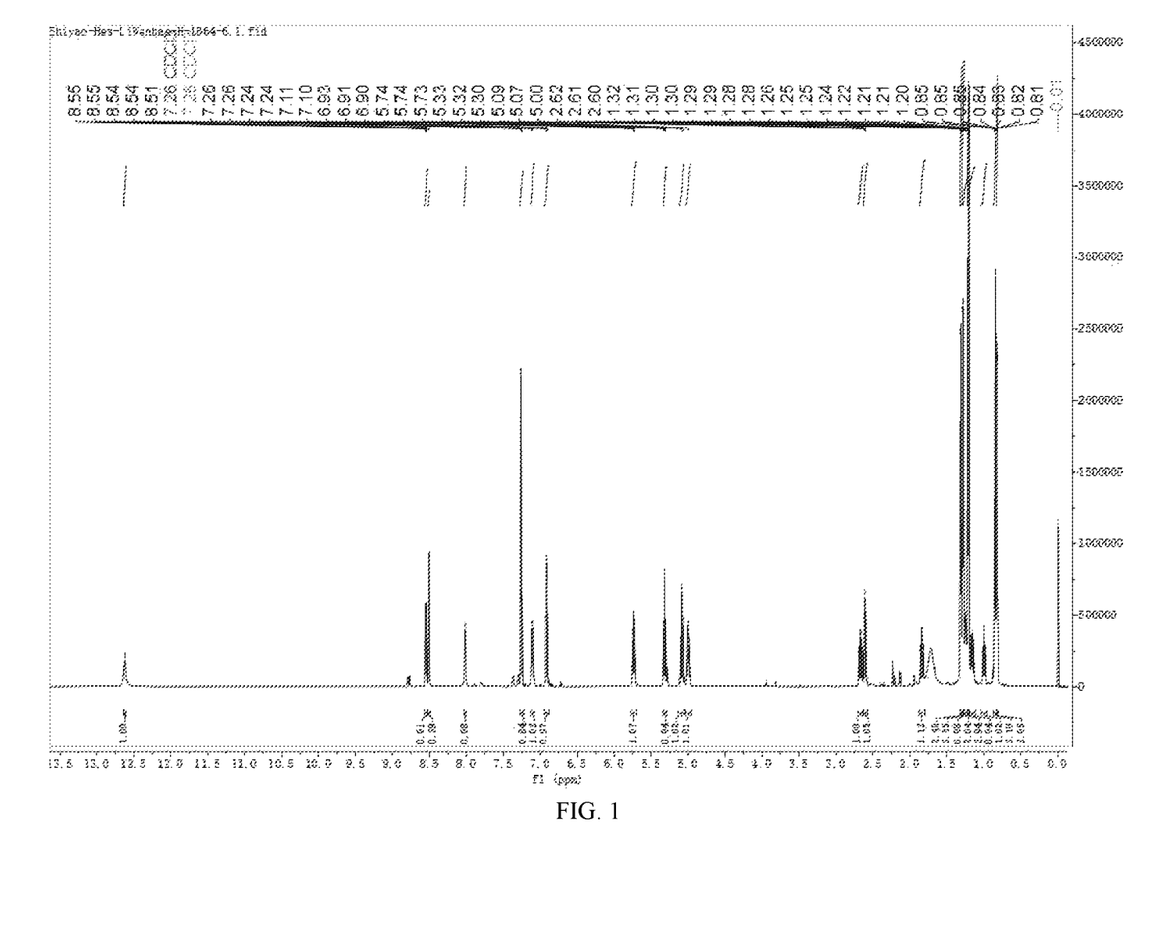
FIG. 1 is an H NMR (nuclear magnetic resonance spectroscopy) spectrum of a compound according to the present invention.
Figure 2:
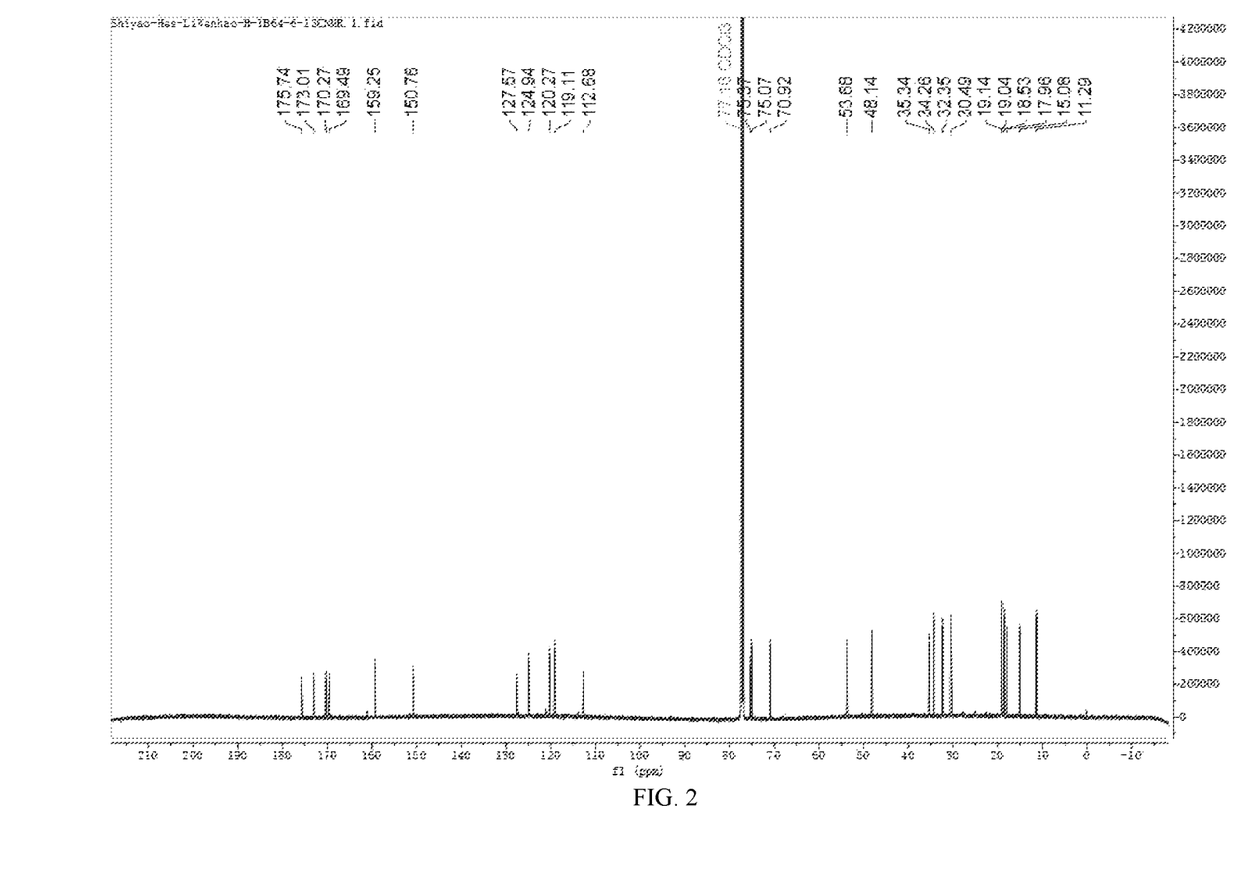
FIG. 2 is a C NMR spectrum of the compound according to the present invention.
Figure 3:
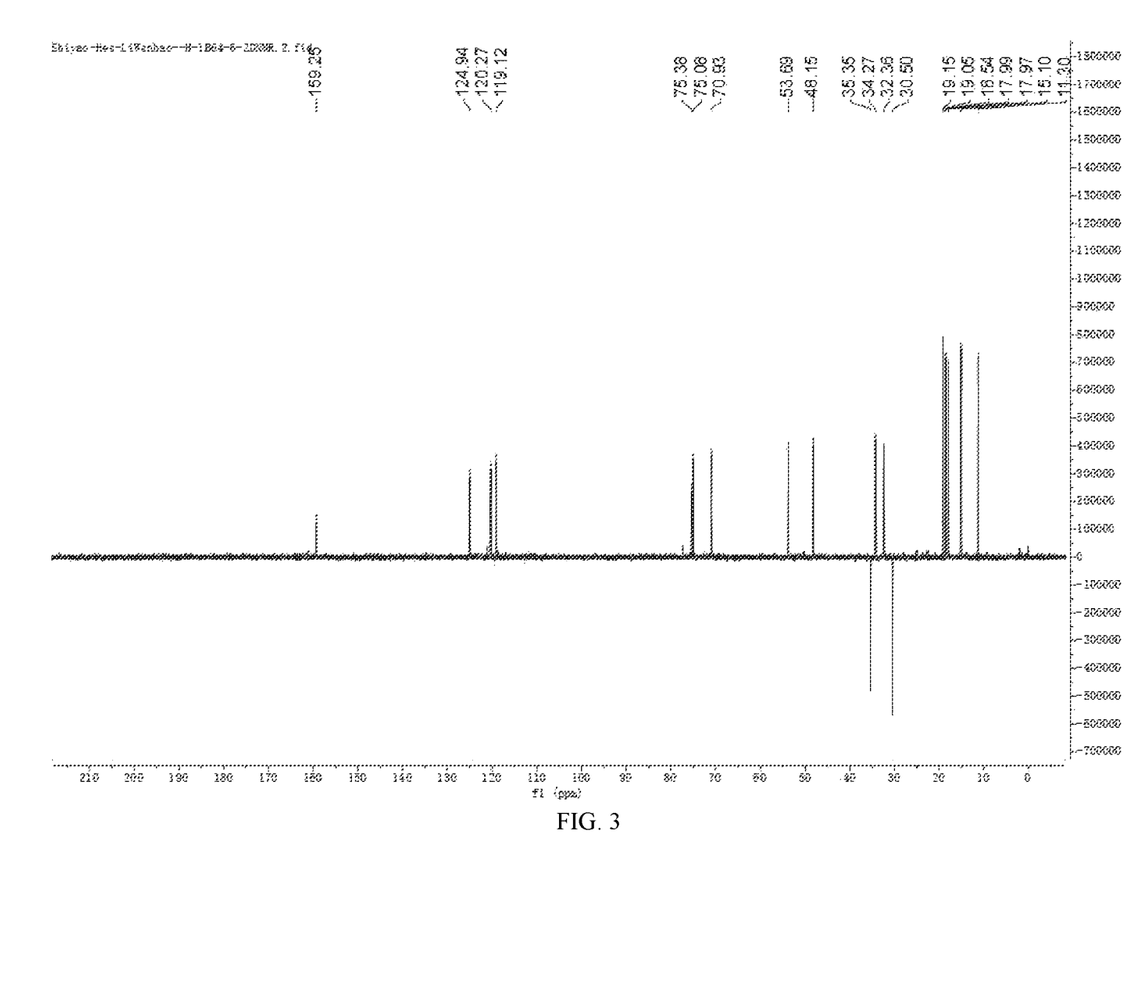
FIG. 3 is a DEPT-135 NMR spectrum of the compound according to the present invention.
Figure 4:
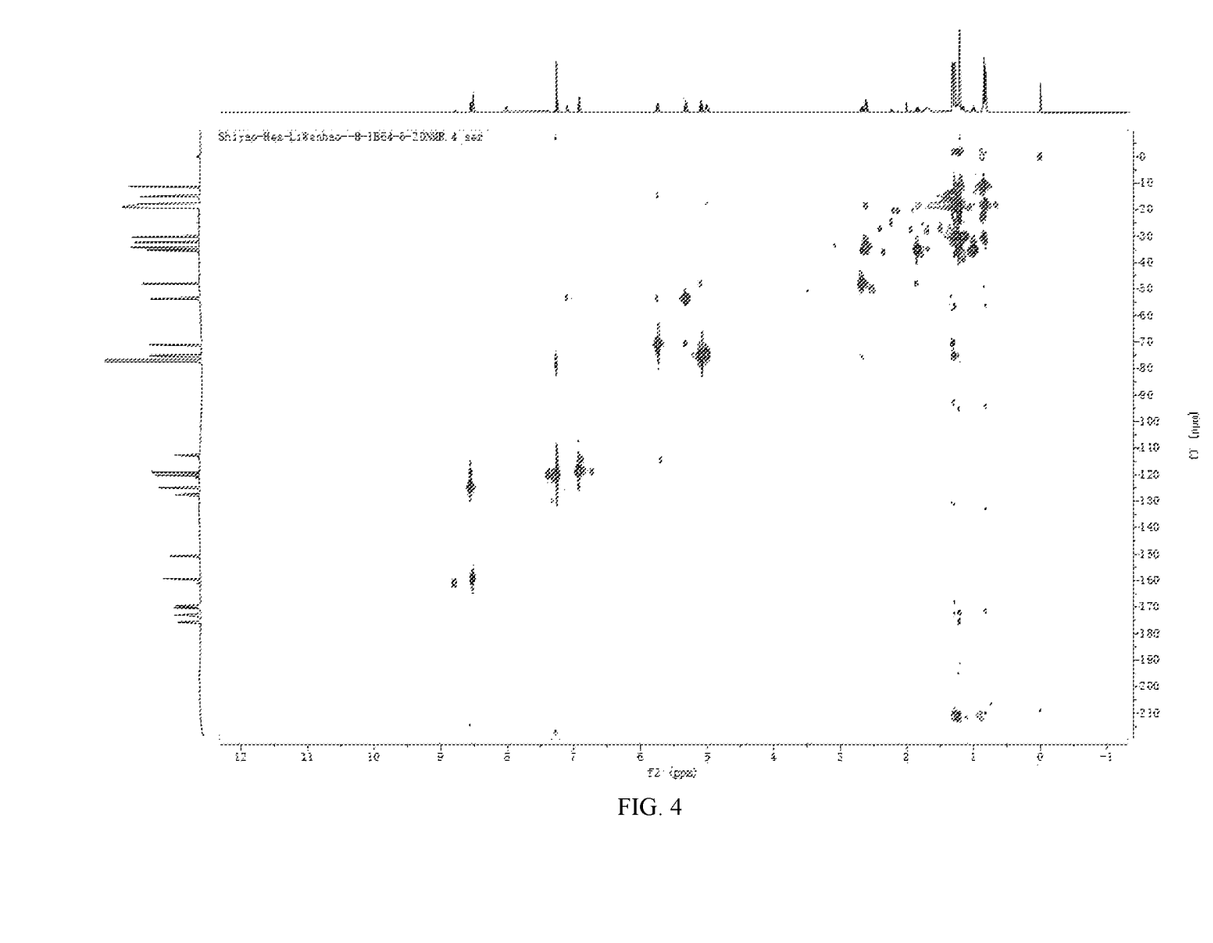
FIG. 4 is an NMR-COSY spectrum of the compound according to the present invention.
Figure 5:
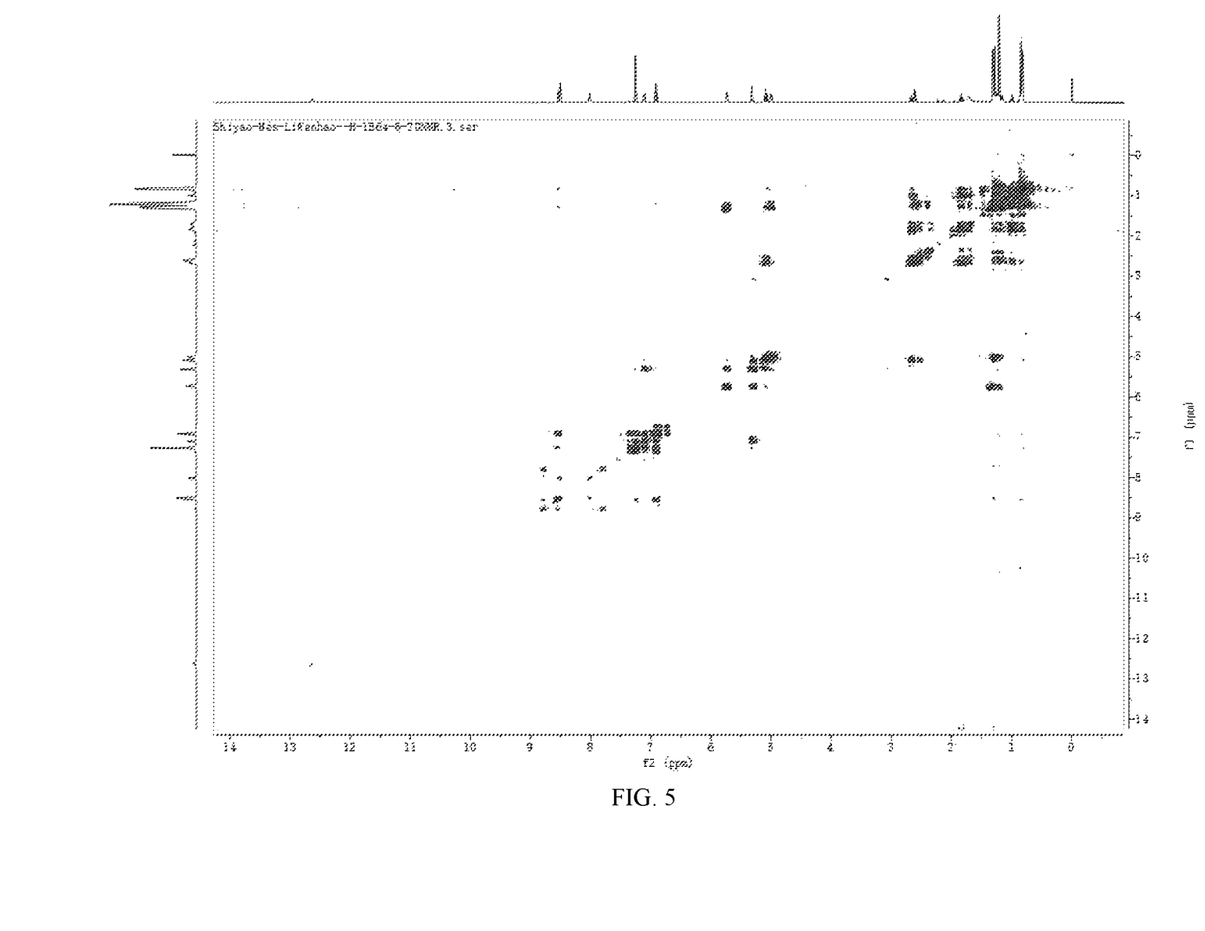
FIG. 5 is an NMR-HSQC spectrum of the compound according to the present invention.
Figure 6:
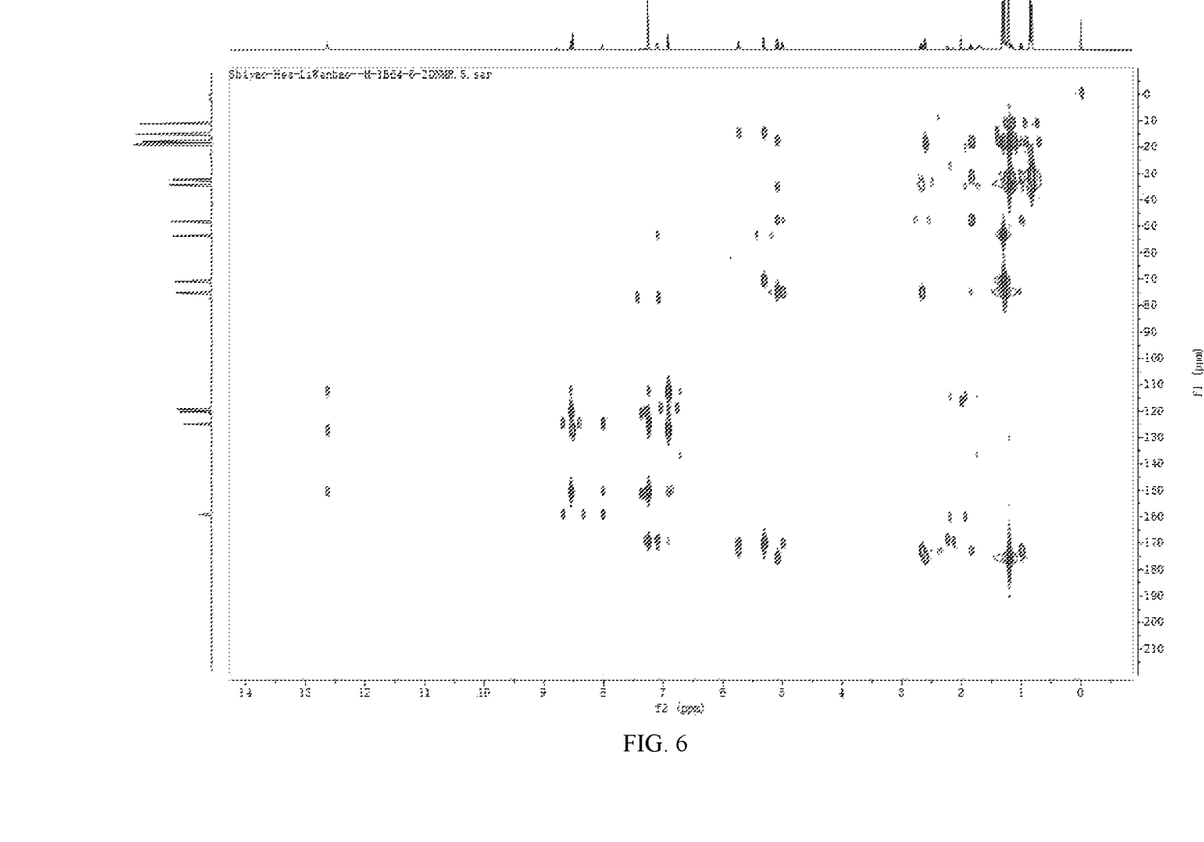
FIG. 6 is an NMR-HMBC spectrum of the compound according to the present invention.
Figure 7:
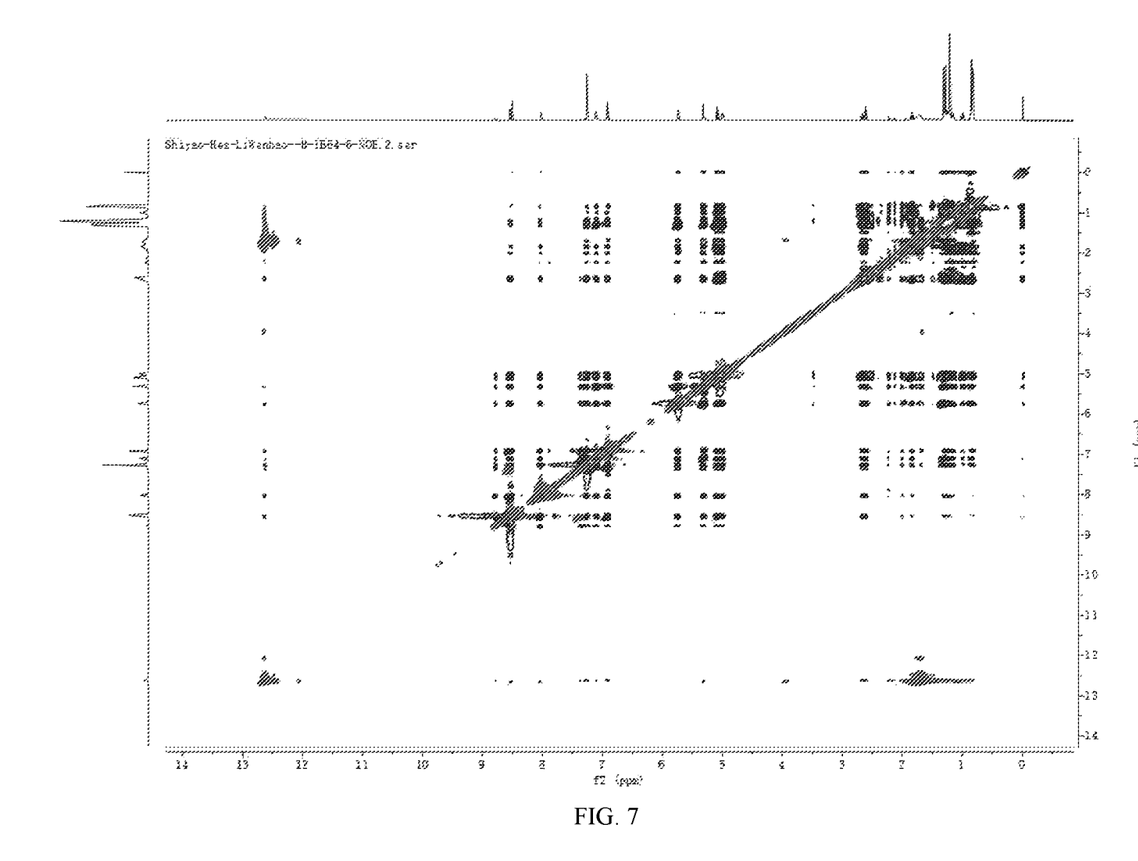
FIG. 7 is an NMR-NOESY spectrum of the compound according to the present invention.
Figure 8:
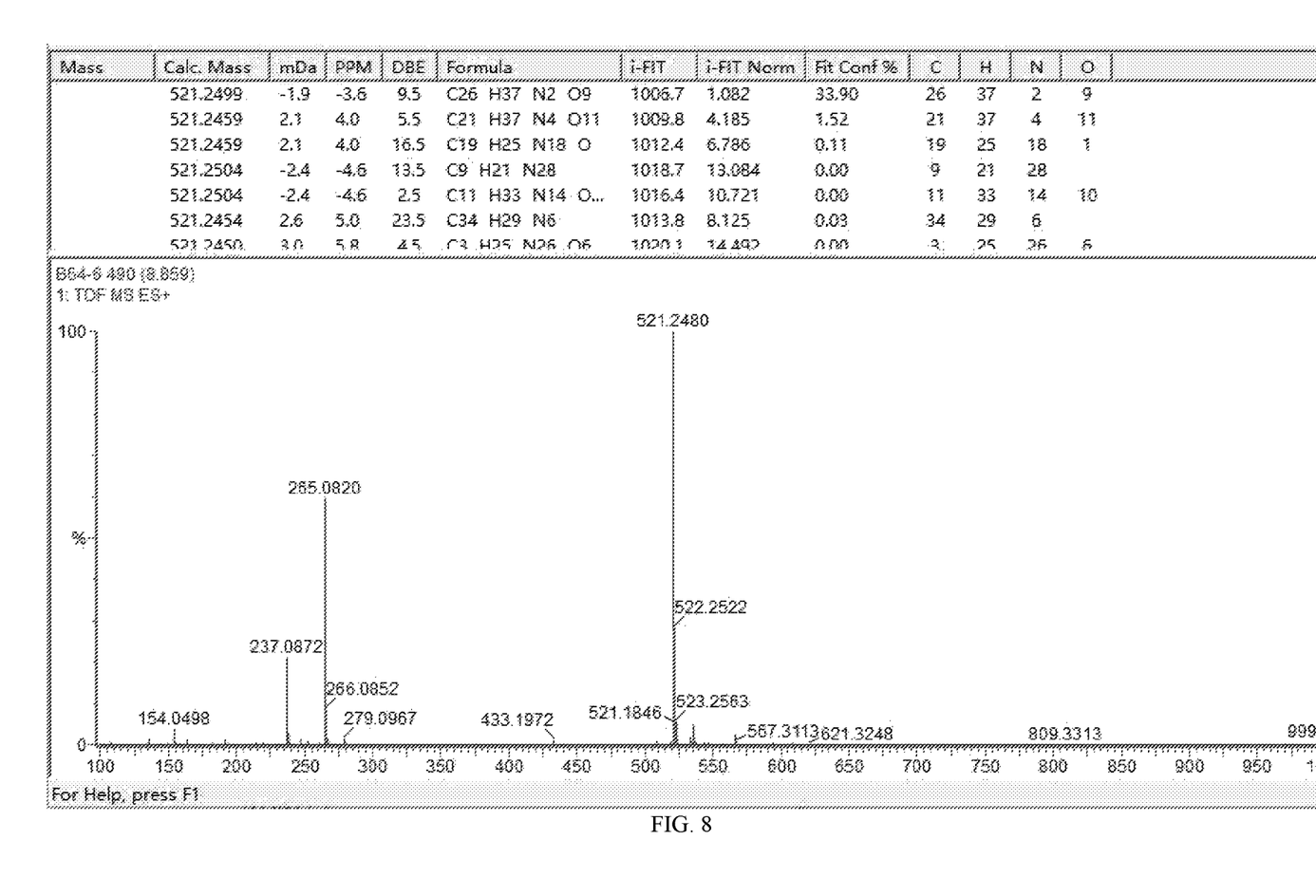
FIG. 8 is a mass spectrum of the compound according to the present invention.
Figure 9:
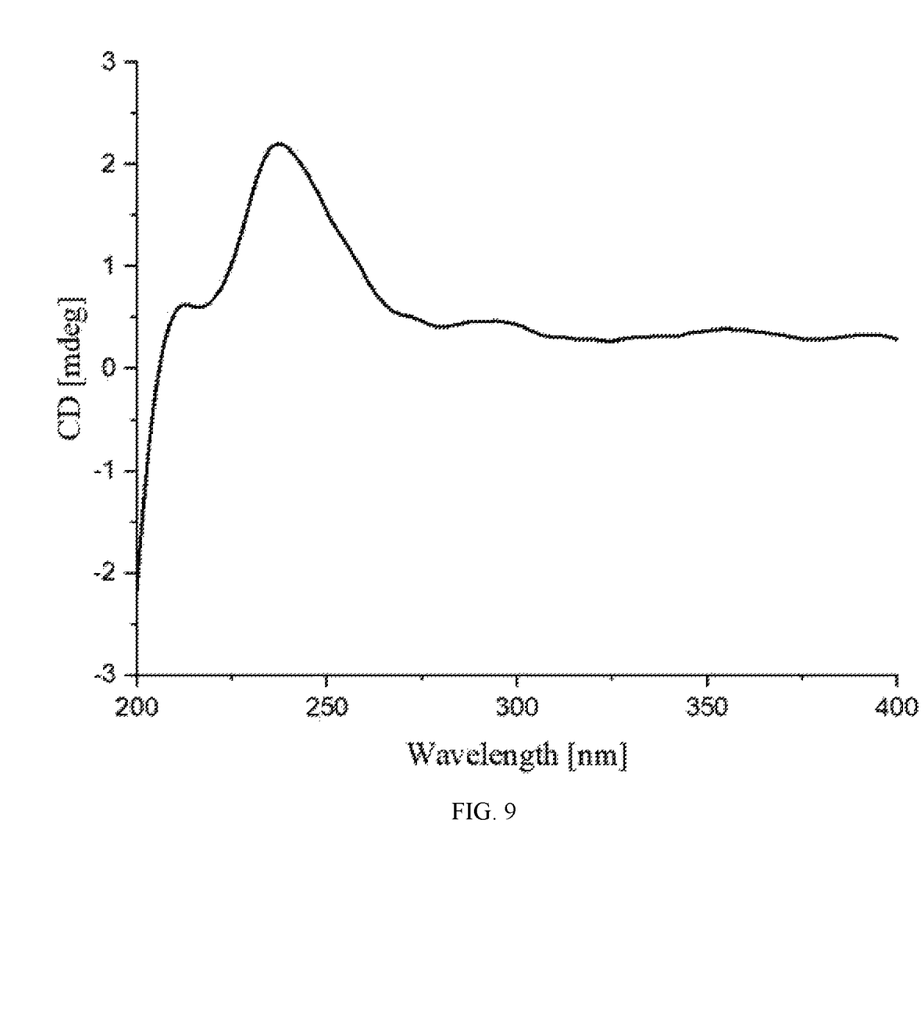
FIG. 9 is an experimental ECD curve diagram of the compound according to the present invention.

Compound I of the present invention was a white powder, and its quasi-molecular ion peak m/z 521.2480 $[M+H]^+$ was given by high-resolution mass spectrometry (HR-ESI-MS) in positive ion mode (FIG. 8). In combination with $^{13}C$ NMR, its molecular formula was determined as $C_{26}H_{37}N_2O_9$, indicating that its degree of unsaturation was 10. Referring to FIGS. 1, 2 and 3 and with the help of $^{13}C$ and $^1H$ NMR data and HSQC data (FIG. 5), 26 carbon resonance peaks were assigned to five carbonyl carbon signals ($\delta_C$ 175.74, 173.01, 170.27, 169.49, and 159.25), six olefin carbon signals ($\delta_C$ 150.76, 127.57, 124.94, 120.27, 119.11, and 112.68), and seven methylene carbon signals ($\delta_C$ 75.37, 75.07, 70.92, 53.68, 48.14, 34.26, and 32.35), two methylene carbon signals ($\delta_C$ 35.34 and 30.49), and six methyl carbon signals ($\delta_C$ 19.14, 19.04, 18.53, 17.96, 15.08, and 11.29). These NMR characteristic signals indicated the existence of antimycin backbone structure. Referring to $^1H$-$^1H$ COSY correlation between NH-3' ($\delta_H$ 8.02) and H-8' ($\delta_H$ 8.51) (FIG. 4) and the HMBC correlation from NH-3' ($\delta_H$ 8.02) to C-8' ($\delta_C$ 159.25), an NH—CHO moiety could be assembled. A set of aromatic spin systems ($\delta_C$ 112.68, $\delta_C$ 150.76, $\delta_C$ 127.57, $\delta_H$ 8.55/$\delta_C$ 124.94, $\delta_H$ 6.91/$\delta_C$ 119.11, and $\delta_H$ 7.25/$\delta_C$ 120.27), as well as HMBC correlations between hydroxyl proton OH-2' ($\delta_H$ 12.62) and the aromatic carbon and between amide proton ($\delta_H$ 8.02) and the aromatic carbon indicated the presence of N-formylaminosalicylic acid moiety. The presence of an isopentyl side chain was indicated by 1H-1H COSY correlations from H-1" to H-7, H-4" to H-3" and H-5" to H-2" as well as HMBC correlations from H-2" to C-1 and H-5" to C-1" and H-5" to C-3". The combination of the 1H-1H COSY correlation from H-2" to H-3" and H-2" to H4" and the HMBC correlation between H-3" and C-1" and between H-8 and C-1" indicated the presence of 2-methylpropionyl (FIG. 6). Considering that five carbonyl signals and one benzene ring account for nine unsaturations, the last unsaturation appeared to be the presence of a single ring. Furthermore, in combination with the remaining NMR data, it was shown that Compound I had a nine-membered bilactone ring that was deduced from the continuous COSY correlation from H-10 to H-1" and from NH-3 to H-11 and the HMBC correlation from protons H-3, H4 and H-9 to carbonyl carbon C-2 and from H4 and H-7 to carbonyl carbon C-6. Finally, HMBC correlation combined the substructures defined above. As shown in the compound of formula (I), the planar structure of Antimycin I was established. The NOESY correlations of H-3/H-4/H-10, NH3/H3-11, H-9/H-7 and H-10/H-1" indicated that they had the same orientation (FIG. 7), but the large coupling constants (9.6-10.0 Hz) between H-7/H-8 and H-8/H-9 indicated that they had different orientations. The CD spectrum of the new Compound I showed that the ECD curve of the quasi-molecular ion peak (FIG. 9) was very close to that of the known antimycin, and it provided clear evidence that the new Compound I had the same absolute conformation as the known antimycin, suggesting that the absolute conformations of the new compound I were 3S, 4R, 7R, 8R and 9S. The $^1H$ and $^{13}C$ NMR spectrum data of this compound are shown in Table 1.

TABLE 1

| 1D NMR data of Compound I (DMSO-d6) | | |
|---|---|---|
| Position | B64-6$\delta_C$ | B64-6$\delta_H$ (J in Hz) |
| 2 | 170.27, C | |
| 3 | 53.68, CH | 5.32, t(7.72) |
| 4 | 70.92, CH | 5.73, m |
| 6 | 173.01, C | |
| 7 | 48.14, CH | 2.66, m |
| 8 | 75.37, CH | 5.09, t(9.96) |
| 9 | 75.07, CH | 5.00, dq(9.72, 6.24) |
| 10 | 17.96, CH$_3$ | 1.28, d(6.14) |
| 11 | 15.08, CH$_3$ | 1.31, d(6.71) |
| 1" | 35.34, CH$_2$ | 0.99, m; 1.84, m |
| 2" | 32.35, CH | 1.25, m |
| 3" | 30.49, CH$_2$ | 1.16, m; 1.25, m |
| 4" | 11.29, CH$_3$ | 0.84, t(7.23) |
| 5" | 18.53, CH$_3$ | 0.82, d(6.35) |
| 1' | 112.68, C | |
| 2' | 150.76, C | |
| 3' | 127.57, C | |
| 4' | 124.94, CH | 8.55, dd(8.02, 1.35) |
| 5' | 119.11, CH | 6.91, t(8.05) |
| 6' | 120.27, CH | 7.25, dd(8.17, 1.37) |
| 7' | 169.49, C | |
| 8' | 159.25, CH | 8.51, d(1.73) |
| 1''' | 175.74, C | |
| 2''' | 34.26, CH | 2.60, h(6.98) |
| 3''' | 19.04, CH$_3$ | 1.21, d(3.84) |
| 4''' | 19.14, CH$_3$ | 1.20, d(3.81) |
| NH-3' | | 8.02, s |
| NH-3 | | 7.11, d(7.67) |
| OH-2' | | 12.62, s |

Note 1:
s—singlet, d—doublet, t—triplet, q—quartet, and m—multiplet.
Note 2:
$^1H$ was obtained by NMR at 600 MHZ; $^{13}C$ was obtained by NMR at 150 MHz.

Example 2

Activity and use of the antimycin compound of Example 1

1. Experimental Sample

Preparation of the test sample solution: The test sample was the pure compound I separated and purified in the above Example 1. An appropriate amount of sample was accurately weighed and mixed with DMSO to obtain a solution of the required concentration for testing the antifungal activity. The indicator bacteria used in this experiment were *Botrytis cinerea* (CGMCC3.3789) and *Penicillium citrinum* (ATCC1109).

2. Experimental Method:

Oxford Cup method for antifungal test: 100 μL of spore suspension was spread evenly on PDA plates, and Oxford cups were placed in the center of the plates. 100 μL of compound solutions of different concentrations were added into the Oxford cups separately, the concentrations of the compound solutions were 32 μg/mL, 16 μg/mL, 8 μg/mL, 4 μg/mL, 2 μg/mL, 1 μg/mL, and 0.5 μg/mL. DMSO was used as a negative control, and prochloraz of the same concentration was used as a positive control. After incubation at 28° C. for 5 days, the growth of fungi was observed. Four culture plates were set up for each treatment, and the whole experiment was repeated three times.

3. Experimental Results

The minimum inhibitory concentration (MIC) of compound I was determined to be 2 μg/ml for *Staphylococcus griseus* (CGMCC 3.3789) and 4 μg/ml for *Penicillium oryzae* (ATCC 1109) in the antifungal test by Oxford Cup method.

The above description does not limit the present invention, and the present invention is not limited to the above examples. Changes, modifications, additions or substitutions made by those of ordinary skill in the art within the essential scope of the present invention should also fall within the scope of the invention.

What is claimed is:

1. A method for obtaining an antimycin compound of formula (I) comprising the following steps:

(1) obtaining a fermentation liquid comprising the antimycin compound by streaking *Streptomyces* sp.4-7 having China Center for Type Culture Collection (CCTCC) deposit number M2020953 on a plate of GAUZE's solid medium No. 1, incubating the *Streptomyces* sp.4-7 in an incubator at 28° C. for 7 days, picking and inoculating single colonies in GAUZE's liquid medium No. 1, placing the GAUZE's liquid medium No. 1 on a shaker for incubation and proliferating the *Streptomyces* sp.4-7 at a temperature of 28° C. and a speed of 180 rpm/min for 3 days, collecting seed liquid comprising the *Streptomyces* sp.4-7 and inoculating a YMG medium with the seed liquid at an inoculation dose of 10% by volume and incubating at 28° C. for 11 days to obtain a fermentation liquid comprising the antimycin compound, wherein the YMG medium is prepared by dissolving 20 g of starch, 10 g of glucose, 5 g of yeast extract, 5 g of malt extract, 0.5 g of calcium carbonate and 30 g of sea salt in 1000 mL of seawater;

(2) extracting the antimycin compound by adding ethyl acetate to the fermentation liquid obtained in step (1), wherein the volume of ethyl acetate added is equal to the volume of the fermentation liquid, wherein the extraction is performed 3 times, combining ethyl acetate phases from the three extractions to obtain an ethyl acetate extract, concentrating the ethyl acetate extract and evaporating the concentrated ethyl acetate extract to dryness to obtain a crude extract; and (3) separating and purifying the antimycin compound by dissolving the crude extract obtained in step (2) in a mixed solvent of dichloromethane and methanol with a volume ratio of 1:1, mixing the resulting solution with 200-300-mesh silica gel to obtain a sample, subjecting the sample to normal-phase medium-pressure liquid chromatography (MPLC) with gradient elution by using an eluent petroleum ether-ethyl acetate solution with volume ratios of 100:1-0:1 and collecting 6 eluted fractions, arranging the 6 eluted fractions in order according to the polarity of the fractions from low to high; subjecting fraction 2 of the 6 eluted fractions to reversed-phase MPLC with gradient elution using an eluent acetonitrile-water solution with volume ratios of 30-100% for 150 min, and collecting 21 eluted fractions, arranging the 21 eluted fractions in order according to the polarity of the fractions from high to low; and separating and purifying fraction 9 of the 21 eluted fractions by semi-preparative reversed-phase high-performance liquid chromatography using a mixed solution of acetonitrile and water with a volume ratio of 24:76 as a mobile phase at a flow rate of 2.0 mL/min, thus obtaining the antimycin compound having formula (I),

* * * * *